United States Patent [19]

Cuming

[11] Patent Number: 5,287,734
[45] Date of Patent: Feb. 22, 1994

[54] THERMAL SENSOR

[76] Inventor: Kenneth J. Cuming, 68 Robinson Rd., Hawthorn, Victoria 3122, Australia

[21] Appl. No.: 13,814

[22] Filed: Feb. 2, 1993

[30] Foreign Application Priority Data

Feb. 13, 1992 [AU] Australia .................... PL0877

[51] Int. Cl.$^5$ .................................... G01N 25/56
[52] U.S. Cl. ............................. 73/75; 374/45
[58] Field of Search .................. 73/75; 374/45

[56] References Cited

U.S. PATENT DOCUMENTS

| | | | |
|---|---|---|---|
| 2,362,344 | 11/1944 | Baver et al. | 73/75 |
| 2,718,141 | 9/1955 | Richards | 73/75 |
| 3,553,481 | 1/1971 | Hasenbeck | 307/118 |
| 3,847,351 | 11/1974 | Hasenbeck | 73/75 |
| 4,059,982 | 11/1977 | Bowman | 73/15 |
| 4,197,866 | 4/1980 | Neal | 137/1 |
| 4,513,608 | 4/1985 | Cuming | 73/73 |
| 4,845,978 | 7/1989 | Whitford | 374/45 |
| 4,886,088 | 12/1989 | Ryokai et al. | 137/78.3 |

FOREIGN PATENT DOCUMENTS

| | | | |
|---|---|---|---|
| 2536777 | 3/1977 | Fed. Rep. of Germany | 73/75 |
| 0035266 | 3/1980 | Japan | 73/75 |
| 0303579 | 3/1972 | U.S.S.R. | 73/75 |
| 0371493 | 5/1973 | U.S.S.R. | 73/75 |
| 0752163 | 7/1980 | U.S.S.R. | 73/75 |
| 1122953 | 11/1984 | U.S.S.R. | 73/75 |

Primary Examiner—Diego F. F. Gutierrez
Attorney, Agent, or Firm—Baker & Daniels

[57] ABSTRACT

A sensor device is shown for detection of soil moisture levels using thermal diffusivity techniques. The sensor device has a porous media in a first zone, a heated temperature sensor arranged within the first zone, a second zone of a thermally conductive dense media containing a second reference temperature sensor, and leads connecting the sensors to a circuit to provide power to the heated temperature sensor and to the second reference temperature sensor. The circuit includes a comparator to compare outputs from the heated temperature sensor to the second reference temperature sensor so as to provide a signal indicative of soil moisture levels when the sensor device is operationally placed to receive soil moisture into the first zone.

18 Claims, 2 Drawing Sheets

THERMAL SENSOR

BACKGROUND OF THE INVENTION

The present invention relates to devices for sensing moisture content in soils and to thereby control the supply of water to desired areas in agricultural and horticultural situations.

U.S. Pat. No. 4,513,608 discloses one form of sensing device having two separate porous zones with a pair of electrodes in each zone thereby forming a current path through the respective porous zones. In use, the device is placed in an in ground position such that ground moisture may move into or from each of the porous zones. The change in electrical resistance in the current path, through the respective porous zones, is then used to indicate ground moisture levels. This device has proved to be accurate and reliable in use, but does suffer from the disadvantage that its manufacture is relatively time consuming and expensive furthermore expensive cermanic materials must be used to maintain accurately uniform porosity levels in the respective porous zones.

There have been other moisture level sensors proposed using various techniques, such as electrical resistance sensing or impedance or capacitance sensing, as the means of moisture level detection, these moisture level sensors introduce their own problems and complications, especially when working in such an hostile environment physically, chemically and biologically as the soil in practical or commercial outdoor applications. Thermal diffusivity has also been proposed as a means of detection and this does have some practical advantages, although previously proposed devices using this technique have certain disadvantages when in use in a practical commercial environment (as opposed to laboratory situations).

The basis of using thermal diffusivity as a detection means is as follows. Transmission of heat energy through a dry porous material is generally poor because the particles only make point contacts where they abut, hence the area for heat flow is necessarily small. As moisture content increases, capillary meniscus form at the points of contact considerably increasing the transfer of heat between particles, as water is a much better conductor of heat than air. The thermal conductivity of the composite will increase significantly with the increase of water content.

As the moisture content increases, air is displaced from the pores and as water has a higher specific heat, the specific heat of the composite also increases.

In a porous material, the rate of dissipation of heat depends on the thermal conductivity, the specific heat and the density. A constant known as "Diffusivity" has been used to relate these properties in an isotropic homogeneous material, when its thermal conductivity does not depend on temperature.

As indicated above, the relationship between Thermal Diffusivity of a porous material and its moisture content has long been used in laboratory situations to monitor moisture content of soils. In an early example, a copper wire heating coil was used, and by measuring resistance change in the same coil over a given heating period, a temperature relationship was established with its diffusivity, (Baver & Shaw 1944 U.S. Pat. No. 2,362,344).

In order to improve robustness of the element and stabilise thermal interface, a separate thermistor type temperature sensor was introduced and encapsulated with the copper coil heater in a standardised medium within a porous ceramic housing (Richards 1955 U.S. Pat. No. 2,718,141).

Although relatively satisfactory in research type applications, that mode of operation could not be applied to automatic irrigation control. An attempt was made based on duplication of devices, with the heat source and temperature sensor being combined in the form of a positive coefficient thermistor coupled to a current sensing relay (Hassenbeck 1971 U.S. Pat. No. 3,553,481). It is unlikely that this would be practical, due to magnitude of the resistance change required to provided minimum current change for reliable relay operation.

A further modification was made using a single device and combining a single thermistor embedded within a porous media of glass beads (Hassenbeck 1974 U.S. Pat. No. 3,847,351). This combination, in conjunction with current threshold sensing, has been employed commercially, although its lack of environmental temperature compensation and the high heat release it required probably limited its accuracy and reliability.

Determination of temperature rise by deducting initial temperature from final temperature after a known amount of heat has been added, change in diffusivity has been calculated in fluids (Bowman 1975 U.S. Pat. No. 4,059,982). This principle was combined with a separate heat source and used with a diode temperature detector in conjunction with timing, storage, combining, comparing and controlling means (Neal 1977 U.S. Pat. No. 4,197,866).

A similar but more specific device is disclosed in U.S. Pat. No. 4,886,088 to Ryokai & Wakabayashi, using energy source, energy level detection and control means.

Most previous attempts to employ thermal diffusivity as a detection means in soil moisture sensing have lacked positive drift free calibration, have not had a matric tension based response, have not had a positive temperature reference or have employed complex detection control means or some combination of the aforementioned.

SUMMARY OF THE INVENTION

The principal objective of the present invention is to provide a simple sensor device for detection of soil moisture content using thermal diffusivity techniques which is reliable and accurate in commercial environments and which is relatively inexpensive to produce. More particularly, the present invention uses the matric tension characteristic of a porous media to provide an accurate matric tension related soil moisture sensing means in combination with a thermal diffusivity detection means involving a heated temperature sensor and a reference temperature sensor, to provide an accurate and simple control means.

Accordingly the present invention provides a soil moisture content sensing device intended in use to be embedded in a soil area to be sensed, said device comprising a porous media forming a first zone, a heated first temperature sensor arranged within said first zone, a second zone of a thermally conductive dense media, and a second reference temperature sensor located within said second zone, said sensors both being adapted for connection to circuit means which includes means to provide power to heat said first temperature sensor, said circuit means including comparator means to compare outputs from said heated first temperature sensor and to said second reference temperature sensor. Preferably the second reference temperature sensor is also heated.

Preferably, said heated diffusivity temperature sensor arranged within said first zone comprises a heating element and a separate temperature sensing element. Alternatively, the heated temperature sensor may comprise a single element such as a thermistor. Conveniently, the second reference temperature sensor also is formed by a thermistor, and preferably when two thermistors are used, they are matched in production to avoid balancing requirements in the control circuitry.

The first and second zones may be constructed separately but are conveniently formed together for ease of handling and installation. The first zone may be formed by discrete particles such as glass beads or the like, and in such a case, a surrounding porous housing of a ceramic material or the like is provided. The first zone may, however, be formed itself by a porous ceramic material. When a porous ceramic material is used as an outer housing, it is necessary that some of the pore sizes of the housing be less than the pore sizes of the media in said first zone. This allows soil moisture to be drawn into the porous media forming the first zone. It is, however, desired to provide suitable means to allow escape of air from the pore voids in the first zone during movement of soil moisture into this zone. One means of achieving this would be the provision of some pore sizes in the housing material that are larger than the pore sizes in the first zone. In a particularly preferred embodiment, the porous housing may be formed as a cylinder and retain both said first and second zones with an isolation wall therebetween, although it is not certain that the isolation wall is absolutely necessary. Preferably, the thermal conductivity of the dense media forming the second zone will be selected so that it is about equal to the thermal conductivity of the first zone, when it is within the range of 25 to 75% (preferably about 50%) filled with soil moisture.

By the terminology "dense" media used herein, it is meant that the media is sufficiently dense to not take up ground moisture as occurs with the porous material of the first zone. Conveniently, the materials are selected so as to have appropriate elasticity and engagement (or bonding) characteristics, so that substantially uniform heat transfer conditions are maintained between the sensors and the surrounding material. That is, air gaps surrounding the sensors during use should not be allowed to form, and also excessive compression on the sensors should not be allowed to form, during use.

BRIEF DESCRIPTION OF THE DRAWINGS

Several preferred embodiments of the present invention will hereinafter be described with reference to the accompanying drawings, in which.

DESCRIPTION OF THE PREFERRED EMBODIMENT

Figure 1:
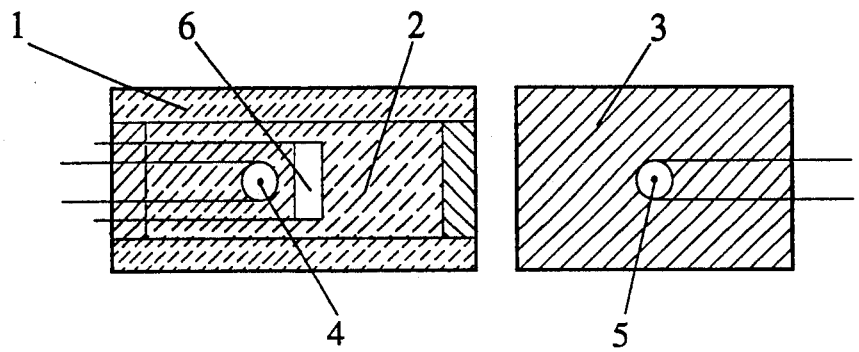
FIG. 1 is a schematic cross-sectional view of a first preferred embodiment of a sensor arrangement according to the present invention.
Figure 2:
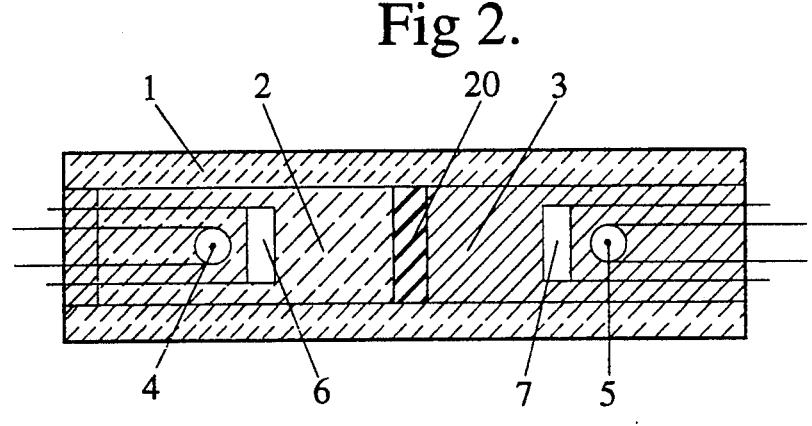
FIG. 2 is a view similar to FIG. 1 showing a second preferred embodiment.

Referring now to FIG. 1, there is shown schematically in cross-section, a basic sensor where an outer cylindrical housing (1) is provided the housing is porous to allow water (ground moisture) to enter or leave a first porous zone (2) formed from a porous media such as glass beads, diatomaceous earth particles, porous ceramic or the like. Embedded within the material forming the first zone (2) is a temperature sensor (4) and a heater element (6), with the sensor (4) and heater element (6) being in close proximity. A second zone (3) is formed from a constant media, which is dense (non porous) and heat conductive. Typically, an epoxy resin might be suitable for this zone. The second zone (3) contains a reference temperature sensor (5) embedded therein. The zones (2) and (3) may be separately formed as illustrated in FIG. 1, or formed as one unit as shown in FIG. 2 by extending the outer porous housing (1) to contain both zones (2) and (3).

Functionally, with careful selection of the construction of the porous housing (1), so that a proportion of its pore voids are smaller than the voids of the detection media in the first zone (2), reliable movement of fluid into and out of the media in the first zone (2) can be achieved. If a proportion of the pore voids in the housing (1) are also larger than the pore sizes in the media in the first zone (2), then a more reliable escape of displaced air can occur. The media in the first zone (2) is selected so that its distribution of smaller pore sizes is such that their capillary breakdown occurs in the desired matric tension range at the desired rate. The moisture within the porous media in the first zone (2) at any time is principally dependent on the capillary tension in the material surrounding the porous housing (1).

A current is passed through the heater (6), which causes the temperature of the sensor (4) to rise. The moisture content of the media in the first zone (2) affects the rate of heat flow away from the heater, causing the temperature at the sensor (4) to rise as the moisture decreases and to fall as it increases.

As little, if any, heat from the heater (6) reaches the reference sensor (5), the difference in temperature between sensors (4) and (5) becomes accurately related to the rate of heat flow away from the heater (6), and therefore in accurate relationship with moisture content of the media (2).

Figure 3:
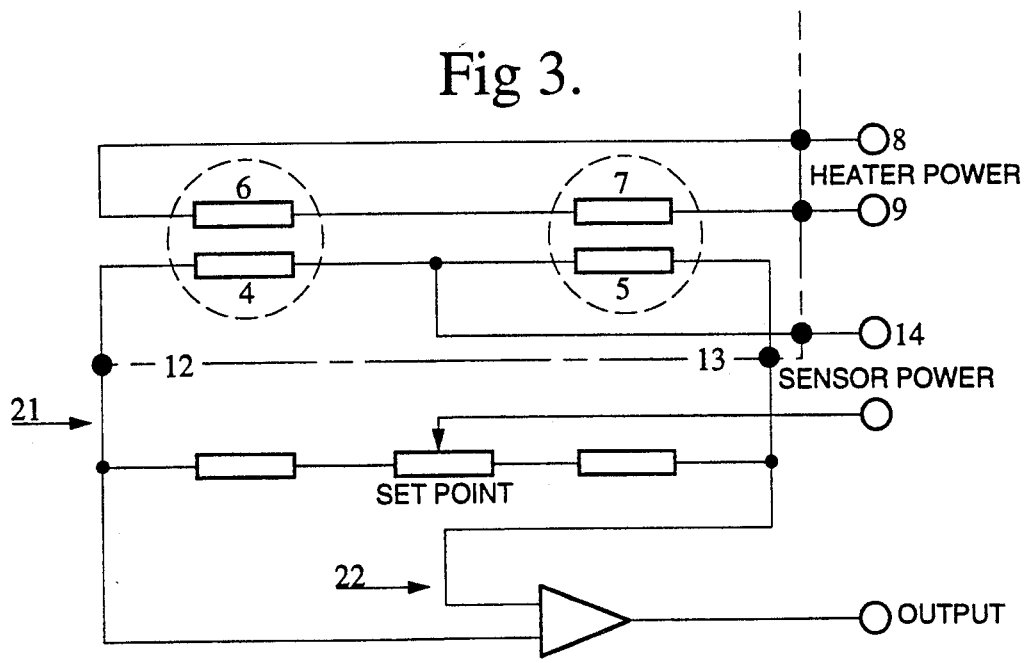
FIG. 3 is a schematic circuit arrangement for the sensor disclosed in FIG. 2.

As shown in FIG. 2, the sensor device may be formed as a single unit, with the housing (1) maintaining the zones (1) and (2) adjacent one another in a predetermined configuration as a single unit. The zones (1) and (2) might, if necessary, be separated by an isolation wall (20). By providing a variation with a separate heater (7) in close proximity to the reference sensor (5), as shown in FIG. 2, advantage can be obtained in some circumstances of detection, as shown in the schematic circuit diagram of FIG. 3. In passing the same current through both heaters, variation in current has less affect on the temperature relationships making resistance of external cables and current control less critical. As shown in FIG. 3, the circuit (21) includes a simple comparator (22). By containing the constant media in the second zone (3) within the same porus housing, the housing component of the thermal diffusivity can be mainly offset.

Figure 4:
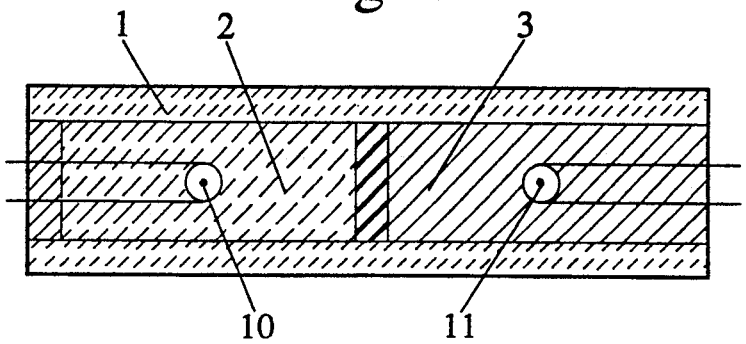
FIG. 4 is a view similar to FIGS. 1 and 2 showing a still further preferred arrangement for the sensor.
Figure 5:
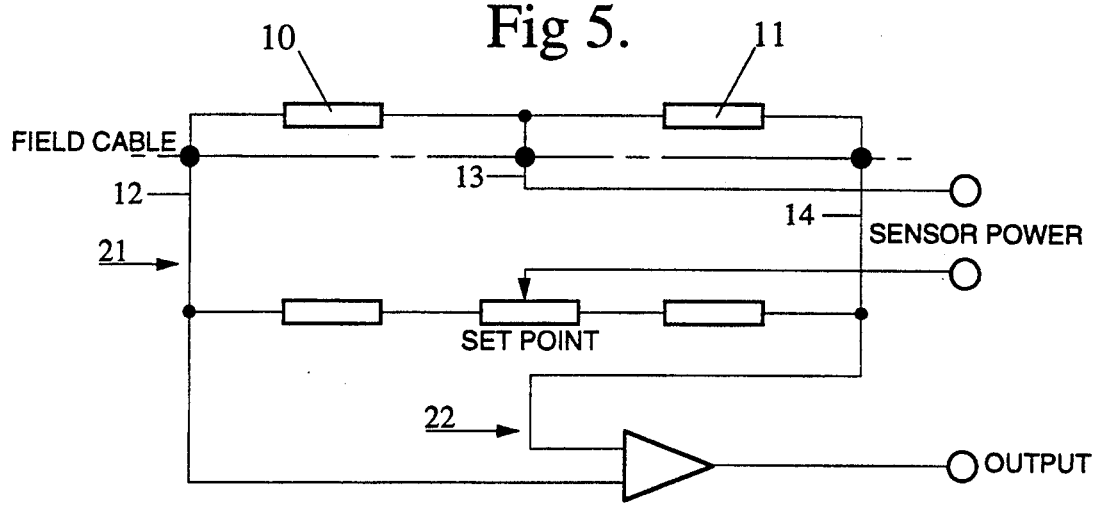
FIG. 5 is a schematic circuit arrangement for the sensor of FIG. 4.

FIG. 4 shows another embodiment which combines the heat source and temperature sensor in one device, for instance a thermistor, IC or diode or the like (shown in FIG. 4 as (10) and (11) the embodiment of FIG. 4 provides practical benefit in ease of assembly, control on proximity of heater and temperature devices, simplification of detection means and reduction in the number of connecting leads to three, as shown in Schematic FIG. 5 as (12), (13) and (14). This is an advantage if the desired detection area is remote from the control apparatus. In production, the conductors to the devices (10),(11) might be lead through the same end wall of the sensor, so that only one cable (containing the conductors) leads from the sensor to the control circuitry. Conveniently, one means of allowing escape of contained air within the porous media of the first zone (2) would be to open the sheath of the cable carrying the conductors to the devices (10),(11) in the first zone (2). In this manner contained air can travel along and within the sheath to be allowed to escape therefrom through appropriately placed apertures in the sheath external of the sensor itself. This might be used in addition to or separate to the enlarged pore sizes (discussed earlier) in the housing (1).

Figure 6:
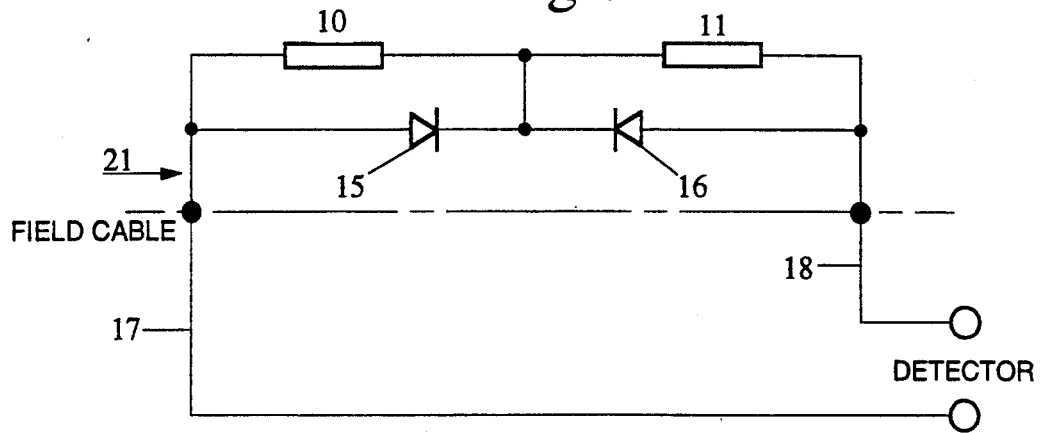
FIG. 6 is a still further circuit arrangement capable of use with the embodiment of FIG. 4.

By providing a variation where reverse blocking diodes (15) and (16) are used as shown in Schematic FIG. 6, a polarity separation can be produced, reducing connecting leads to (17) and (18). Also in an irrigation system, a control common could be used for one lead making only one lead specific to the sensor. An additional advantageous feature involves the sensor circuit (21) which could be energised at irrigation valve voltage.

I claim:

1. A soil moisture content sensing device intended in use to be embedded in a soil area to be sensed, said device comprising a porous media forming a first zone, a heated first temperature sensor arranged within said first zone, a second zone of a thermally conductive non-porous media, and a second reference temperature sensor located within said second zone, said sensors being connected to circuit means which includes means to provide power to heat said first temperature sensor, said circuit means including comparator means to compare outputs from said heated first temperature sensor and said second reference temperature sensor.

2. A soil moisture content sensing device according to claim 1 wherein said second reference temperature sensor is also heated.

3. A soil moisture content sensing device according to claim 2 wherein said heated first temperature sensor comprises a heating element and a separate temperature sensing element.

4. A soil moisture content sensing device according to claim 2 wherein said heated first temperature sensor comprises a first thermistor.

5. A soil moisture content sensing device according to claim 2 wherein the second reference temperature sensor comprises a second thermistor.

6. A soil moisture content sensing device according to claim 2 wherein the first and second zones are held in a predetermined configuration adjacent one another by an outer housing structure.

7. A soil moisture content sensing device according to claim 2 further including means to allow contained air to escape from the first zone during hydration of said first zone.

8. A soil moisture content sensing device according to claim 2 wherein the non-porous media forming the second zone has a thermal conductivity about equal to the thermal conductivity of said first zone when the zone contains between 25 and 75% of its maximum soil moisture capacity.

9. A soil moisture content sensing device according to claim 8 wherein the thermal conductivity of said second zone is about equal the thermal conductivity of said first zone when it is about half filled with soil moisture.

10. A soil moisture content sensing device according to claim 1 wherein said heated first temperature sensor comprises a heating element and a separate temperature sensing element.

11. A soil moisture content sensing device according to claim 1 wherein said heated first temperature sensor comprises a first thermistor.

12. A soil moisture content sensing device according to claim 1 wherein the second reference temperature sensor comprises a second thermistor.

13. A soil moisture content sensing device according to claim 1 wherein the first and second zones are held in a predetermined configuration adjacent one another by an outer housing structure.

14. A soil moisture content sensing device according to claim 13 wherein the outer housing structure includes or is formed by a porous material wherein at least some pore sizes of the porous housing material are less than pore sizes of the porous media in said first zone.

15. A soil moisture content sensing device according to claim 1 further including means to allow contained air to escape from the first zone during hydration of said first zone.

16. A soil moisture content sensing device according to claim 15 wherein said means to allow contained air to escape from said first zone includes arranging some of the pore sizes of the porous housing material to be larger than the pore sizes of the porous media in said first zone.

17. A soil moisture content sensing device according to claim 1 wherein the non-porous media forming the second zone has a thermal conductivity about equal to the thermal conductivity of said first zone when the zone contains between 25 and 75% of its maximum soil moisture capacity.

18. A soil moisture content sensing device according to claim 17 wherein the thermal conductivity of said second zone is about equal the thermal conductivity of said first zone when it is about half filled with soil moisture.

* * * * *